United States Patent [19]

Hammond, III et al.

[11] 4,385,843
[45] May 31, 1983

[54] SAMPLE HEATER FOR NON-DESTRUCTIVELY DETERMINING THE COMPOSITION OF AN UNKNOWN MATERIAL SAMPLE

[75] Inventors: Ogden H. Hammond, III, Belmont; John T. Wroclawski, Framingham, both of Mass.

[73] Assignee: The Hetra Corporation, Newport, R.I.

[21] Appl. No.: 234,891

[22] Filed: Feb. 17, 1981

[51] Int. Cl.³ .......................................... G01N 25/00
[52] U.S. Cl. .................................................. 374/43
[58] Field of Search ............... 73/15 R, 15 A, 15 FD; 219/10.77, 10.79; 374/43

[56] References Cited

U.S. PATENT DOCUMENTS

| | | | |
|---|---|---|---|
| 1,869,336 | 7/1932 | De Forest | 73/15 X |
| 3,020,745 | 2/1962 | Sielicki | 73/15 |
| 3,222,917 | 12/1965 | Roth | 73/15 |
| 3,761,667 | 9/1973 | Walden | 219/10.77 X |
| 3,981,175 | 9/1976 | Hammond | 73/15 |
| 4,109,508 | 8/1978 | Fukuyama | 73/15 |
| 4,163,884 | 8/1979 | Kobetsky | 219/10.79 X |

*Primary Examiner*—Herbert Goldstein

[57] ABSTRACT

A system for determining whether a bar of precious metal has a purity of composition which is within a given range of variance. Heat is induced in one end of the bar using an induction heater powered by a high frequency power source, and the time vs. temperature response at the other end of the bar is monitored.

4 Claims, 2 Drawing Figures

SAMPLE HEATER FOR NON-DESTRUCTIVELY DETERMINING THE COMPOSITION OF AN UNKNOWN MATERIAL SAMPLE

BACKGROUND OF THE INVENTION

This invention relates to determining, by nondestructive test methods, the purity of composition of bars of material of a given shape; and more particularly, to determining whether a bar of precious metal has a purity of composition which is within a given range of variance from that of a standard bar of known purity of composition.

U.S. Pat. No. 3,981,175, issued Sept. 21, 1976 (hereby expressly incorporated by reference), discloses an apparatus for making such a nondestructive determination, wherein a standard bar, of known purity of composition, and a sample bar, whose purity of composition is desired, are both placed in a thermal chamber. A heat pulse of finite duration is applied to one end of both bars and the temperature vs. time responses of the opposite ends of both bars are monitored to determine the similarity of response.

In a copending application "Improved Method of and Apparatus for Nondestructively Determining the Composition of an Unknown Material Sample" filed by Ogden H. Hammond III, is described an improved method and apparatus for sequential monitoring, wherein the heat pulse is first applied to one end of the standard bar and the temperature vs. time response of the other end of the standard bar is measured, at specified instants of time, and stored. One end of a sample bar is then subjected to the same heat pulse and the temperature of the other end of the sample bar is measured at the same specified instants of time, relative to the application of the heat pulse. The temperature responses of the two bars are then used to make a decision as to the purity of composition of the sample bar.

The principal object of the present invention is to provide an improved noncontact bar heater, which due to the absence of contact resistances, is capable of producing a constant specified amount of heat rise in different bars, in a short period of time.

SUMMARY OF THE INVENTION

In one aspect, the invention features an induction heater, adjacent a material sample, for causing current flow in the sample.

In preferred embodiments, the induction heater includes a ferromagnetic structure and a coil inductor adjacent the structure, and a capacitor and the coil structure forming a resonant circuit.

DESCRIPTION OF THE PREFERRED EMBODIMENT

We turn now to a description of the preferred embodiment, after first briefly describing the drawings.

Figure 1:
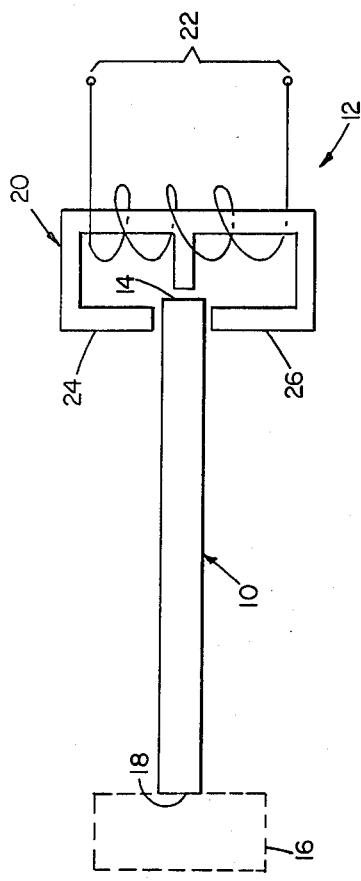
FIG. 1 is a simplified representation of an alternate embodiment of a bar heater, used in a device for determining the thermal characteristics of a material sample.

Referring now to FIG. 1, bar 10, either a standard bar or a sample bar whose thermal characteristics are desired, is positioned so as to contact bar heater 12, at its one end 14, and bar sensor 16, at its other end 18. Since the time vs. temperature response sensed by sensor 16 will depend on the amount of heat applied at end 14, it is desirable that a constant, specified amount of heat be consistently applied to all bars. Use of a standard contact heater for heater 12 has the drawback that, even through the bars may be machined to close tolerances, there will still exist, in different bars, variations in surface irregularities which will cause contact resistances to vary among bars.

Figure 2:
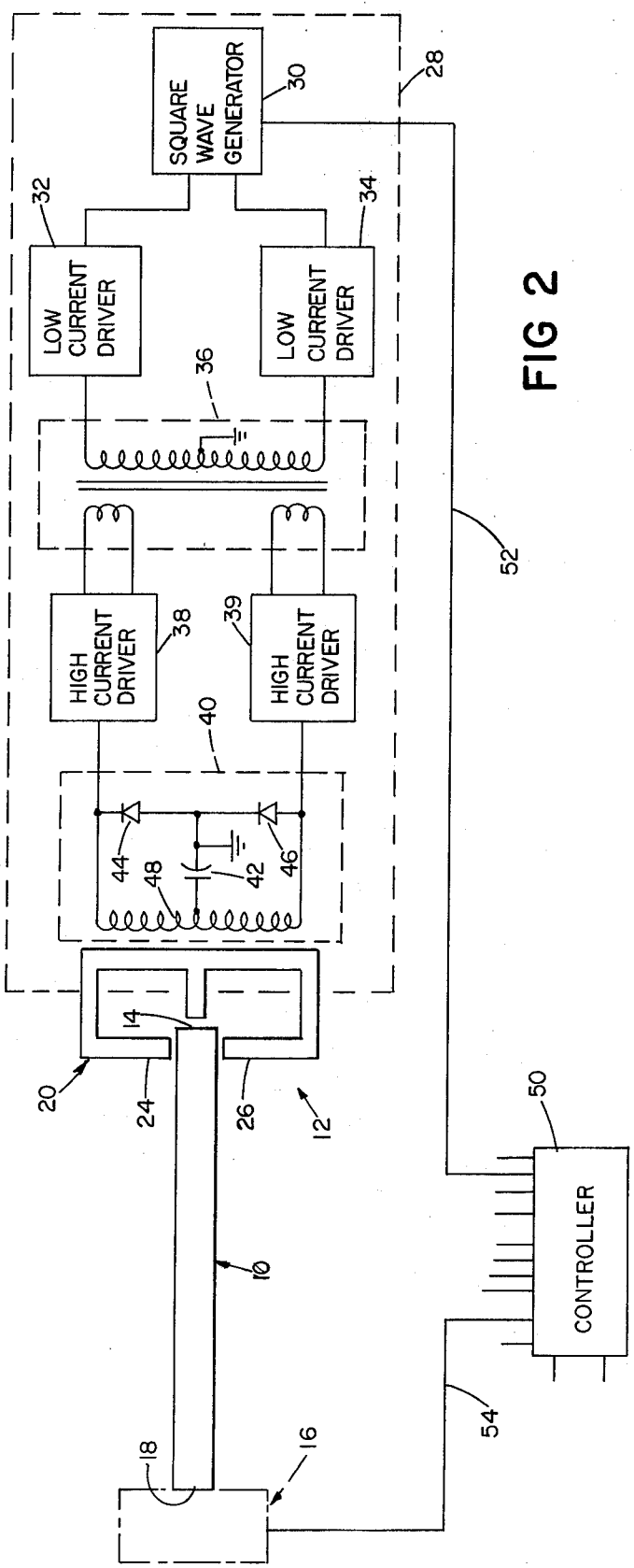
FIG. 2 is a block diagram showing the bar heater at FIG. 1 and its associated electrical circuitry.

I have discovered that variation in contact resistance can be eliminated by use of the noncontact bar heater 12 shown in FIGS. 1 and 2.

Referring still to FIG. 1, coil structure 20 is wrapped with heater power supply line 22 and has extensions 24 and 26 which terminate adjacent end 14 of bar 10. In operation, alternating current flowing through line 22 induces a magnetic field in structure 20. The magnetic field is directed, by extensions 24 and 26, to create a flux field through the end of bar 10. Due to the alternating current supplied by line 22, the flux field through the end of the bar will also alternate, causing repeatedly reversing polarization of bar 10 and corresponding electron flow. Bar 10 will be heated by the current induced in it, according to the $I^2R$ principle of power consumption, where I is the induced current and R is the resistivity of the bar.

Referring now to FIG. 2, line 22 is supplied with a high voltage, high current power supply 28, having a square wave generator 30, low current drivers 32 and 34, a low to high voltage transformer 36, high current drivers 38 and 39, and an RC resonant driving circuit 40. Circuit 40, in turn, consists of a capacitor 42, diodes 44 and 46 and a coil inductor 48, which is wrapped around structure 20.

In operation, generator 30 generates, and supplies to drivers 32 and 34, two square waves which are 180° out of phase. These are amplified by drivers 32 and 34 and supplied to transformer 36 which, in turn, supplies drivers 38 and 39 with a higher voltage level, square wave signal. Drivers 38 and 39 supply, to circuit 40 an alternating, high voltage, high current square wave signal The radial depth of heating induced in bar 10 will, in general, be a function of the frequency of the square wave signal supplied to circuit 40. To a certain extent, the axial distance along bar 10 which is heated will also depend on this same frequency. I have found that high voltage, high current square wave frequencies in the range of 1 to 100 kHz are to be preferred.

Capacitor 42 is chosen to match coil inductor 48, so as to give curcuit 40 a low impedance at the frequency of the square wave signal. Due to the reactance of coil inductor 48 and capacitor 42, the current flow through coil inductor 48, and therefore, the magnetic field induced in structure 20, is increased.

Controller 50, which may be any sort of timed logic device, activates square wave generator 30, through line 52, and reads sensor 16 through line 54.

Other embodiments are within the following claims.

We claim:

1. In a system for determining whether a sample of precious metal has a purity of composition that is within a given range of variance from that of a standard sample of known purity of composition, said system including means for applying a finite heat pulse to a first point of said sample and monitoring the temperature vs. time response of a second point of said sample, that improvement wherein said means for applying said finite heat pulse includes an induction heater disposed adjacent said first point for inducing a flow of current in said sample adjacent said first point in response to the application of alternating current to said heater, and means for applying said alternating current to said heater at a frequency of not less than 1 kHz, said induction heater comprising a ferromagnetic structure for inducing a magnetic flux field through said sample, and a coil inductor adjacent saidstructure for inducing a magnetic field in said structure.

2. The improvement of claim 1, further comprising a capacitor in serial electrical connection with said coil inductor, said capacitor and said inductor comprising a resonant circuit.

3. In a system for determining whether a sample of precious metal has a purity of composition that is within a given range of variance from that of a standard sample of known purity of composition, said system including means for applying a finite heat pluse to a first point of said sample and monitoring the temperature vs. time response of a second point of said sample, that improvement wherein said means for applying said finite heat pulse includes an induction heater disposed adjacent said first point for inducing a flow of current in said sample adjacent said first point in response to the application of alternating current to said heater, and means for applying said alternating current to said heater at a frequency of not less than 1 kHz, said alternating current being in the form of a square wave.

4. The system of claim 3 wherin said frequency of alternating current is in the range of 1 to 100 kHz.

* * * * *